United States Patent [19]

Tenud

[11] 4,018,821
[45] * Apr. 19, 1977

[54] PROCESS FOR THE PRODUCTION OF CARNITINE

[75] Inventor: Leander Tenud, Visp, Switzerland

[73] Assignee: Lonza Ltd., Gampel, Switzerland

[ * ] Notice: The portion of the term of this patent subsequent to July 13, 1993, has been disclaimed.

[22] Filed: Sept. 25, 1975

[21] Appl. No.: 616,849

[30] Foreign Application Priority Data

Sept. 25, 1974 Switzerland .................. 012971/74

[52] U.S. Cl. .................. 260/534 M; 260/482 R
[51] Int. Cl.² .............. C07C 101/10; C07C 101/12
[58] Field of Search .................. 260/534 M

[56] References Cited

UNITED STATES PATENTS

| | | | |
|---|---|---|---|
| 2,530,627 | 11/1950 | Pfister et al. | 260/534 M |
| 2,933,522 | 4/1960 | Cramer et al. | 260/534 M |
| 3,038,007 | 6/1962 | Reeve | 260/534 M |
| 3,135,788 | 6/1964 | Noguchi et al. | 260/534 M |

OTHER PUBLICATIONS

D'Alo et al., "Chem. Abstracts", vol. 60 (1964), cols. 10777, 10778.

Primary Examiner—Joseph E. Evans
Attorney, Agent, or Firm—Fisher, Christen & Sabol

[57] ABSTRACT

The process for the production of carnitine hydrochloride which involves placing an ester of γ-halo-acetoacetic acid having the formula:

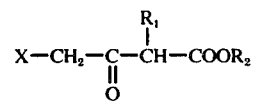

wherein $R_1$ is hydrogen, $R_2$ is a lower alkyl group having 1 to 10 carbon atoms and X is a halogen atom selected from the group consisting of chlorine or bromine, in an aqueous solution of excess trimethyl amine held at a temperature between 0° and 50° C., a reaction resulting between said ester and said amine. The excess trimethyl amine is distilled off. The pH of the solution is adjusted between 4 and 8, (3-carbalkoxy-2-oxopropyl)-trimethyl ammonium halide resulting. The (3-carbalkoxy-2-oxopropyl)-trimethyl ammonium is hydrogenated without isolating said halide from solution, a carnitine ester resulting. The carnitine ester is converted by means of aqueous hydrochloric acid into carnitine hydrochloride.

14 Claims, No Drawings

PROCESS FOR THE PRODUCTION OF CARNITINE

BACKGROUND OF THIS INVENTION

1. Field of This Invention

This invention relates to a process for the production of carnitine hydrochloride.

2. Prior Art

It is known to produce carnitine from acetoacetic ester. At the same time bromoacetoacetic ester is produced by bromation, the latter is converted by means of $NaBH_4$ to $\beta$-hydroxy-$\gamma$bromobutyric acid ester. The latter is reacted with trimethylamine and the developing $\gamma$-trimethylammonium-$\beta$-hydroxybutyric acid ester bromide is saponified into carnitine hydrochloride [F, D'Alo and A. Masserini, Chemical Abstracts, Vol 60, 10777 g (1964) ]. Because of the reduction with sodium borohydride, this synthesis will probably remain limited for economic reasons merely to laboratory scale; moreover the yields are low.

It is known to use epichlorohydrin as a starting material. In such case, one proceeds in such a way that epichlorohydrin is first of all reacted with trimethylaminehydrochloride, the reaction product is converted with NaCN into the carnitine nitrile chloride and the latter is hydrolyzed to carnitine (see U.S. Pat. No. 3,135,788). In such process the products of all the intermediate steps are isolated. The yield amounts to about 74 percent.

The proposal has also been made to convert $\gamma$-chloroacetoacetic acid anilide by reaction with trimethyl amine in an organic solvent, e.g., ethanol, into $\gamma$-trimethyl ammonium acetoacetic acid anilide chloride, to hydrogenate the latter to $\gamma$-trimethyl ammonium $\beta$-hydroxy-butyric acid anilide chloride and then to convert the latter by means of aqueous hydrochloric acid into carnitine hydrochloride. A disadvantage of such a process lies in the fact that one must start out with $\gamma$-chloroacetoacetic acid anilide, which must be produced in a preliminary step from $\gamma$-chloroacetoacetic acid chloride. If in such a process one uses, instead of $\gamma$-chlorocetoacetic acid anilide, $\gamma$-chloroacetoacetic ester, then a mixture of various products develops, that is, mainly trimethylaminohydrochloride and succinylosuccinic acid ester.

BROAD DESCRIPTION OF THIS INVENTION

An object of this invention is to produce carnitine hydrochloride in a good yield by means of a multi-step process that does not require isolation of the products of the intermediate steps of such process. Other objects and advantages of this invention are set out herein or are obvious to one ordinarily skilled in the art herefrom. This invention achieves such objects and advantages.

It has now been found that very good yields of carnitine can be obtained from $\gamma$-halo acetoacetic ester.

This invention involves a process for the production of carnitine hydrochloride which includes placing an ester of $\gamma$-halo-acetoacetic acid having the formula:

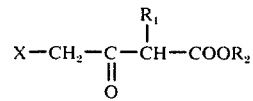

wherein $R_1$ is hydrogen, $R_2$ is a lower alkyl group having 1 to 10 carbon atoms and X is a halogen atom selected from the group consisting of chlorine or bromine, in an aqueous solution of excess trimethyl amine held at a temperature between 0° and 50° C., a reaction resulting between said ester and said amine. The excess timethyl amine is distilled off. The pH of the solution is adjusted to between 4 and 8, (3-carbalkoxy-2-oxopropyl)-trimethyl ammonium halide resulting. The (3-carbalkoxy-2-oxopropyl)- trimethyl ammonium halide is hydrogenated without isolating said halide from solution, a carnitine ester resulting. The carnitine is converted by means of aqueous hydrochloric acid into carnitine hydrochloride, which has the formula:

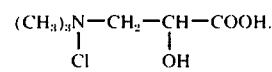

The process of this invention is distinguished by the fact, that it is a so called "one course " process, that is to say the products of the individual steps do not need to be isolated.

DETAILED DESCRIPTION OF THIS INVENTION

The process of this invention is characterized by the fact that $\gamma$-haloacetoacetic ester is inserted into a prepared aqueous trimethylamine solution held at a temperature of 0° to 50° C., the excess trimethylamine is distilled off, the solution is adjusted to a pH value of 4 to 8, (3-carbalkoxy-2-oxopropyl)- trimethyl ammonium chloride resulting, the (3-carbalkoxy-2-oxopropyl)- trimethyl ammonium chloride is hydrogenated without isolating it from the solution, and the carnitine ester is converted by means of an aqueous hydrochloric acid into carnitine hydrochloride.

Examples of useful $\gamma$-haloacetoacetic esters, where $R_1$ is a hydrogen atom, are the methyl ester of $\gamma$-chloroacetoacetic acid, the ethyl ester of $\gamma$-chloroacetoacetic acid, the n-propyl ester of $\gamma$-chloroacetoacetic acid, the isopropyl ester of $\gamma$-chloroacetoacetic acid, the n-butyl ester of $\gamma$-chloroacetoacetic acid, the isopentyl ester of $\gamma$-chloroacetoacetic acid, the n-hexyl ester of $\gamma$-chloroacetoacetic acid, the n-decyl ester of $\gamma$-chloroacetoacetic acid, the 4-methyl-1-heptyl ester of $\gamma$-chloroacetoacetic acid, the 2,3-dimethyl-1-butyl ester of $\gamma$-chloroacetoaceitc acid, the methyl ester of $\gamma$-bromoacetoacetic acid, the ethyl ester of $\gamma$-bromoacetoacetic acid, the n-propyl ester of $\gamma$-bromoacetoacetic acid, the n-hexyl ester of $\gamma$-bromoacetoacetic acid, the isopropyl ester of $\gamma$-bromoacetoacetic acid, the isohexyl ester of $\gamma$-bromoacetoacetic acid, the ethyl ester of $\gamma$-fluoroacetoacetic acid, and the ethyl ester of $\gamma$-iodoacetoacetic acid.

Preferably the $\gamma$-haloacetoacetic ester is a $\gamma$-chloroacetoacetic ester. The preferred esters moieties have 1 to 4 carbon atoms.

$R_2$ can be a lower alkyl group containing one to 10 carbon atoms, which can be straight chain or branch chain alkyl group (Preferably $R_2$ is a lower alkyl having 1 to 4 carbon atoms and is most preferably methyl, ethyl, propyl or butyl - ethyl is most preferred). Examples of useful alkyl groups which $R_2$ can be are: methyl, ethyl, n-propyl, isopropyl, n-butyl, isobutyl, n-pentyl, isopentyl, n-hexyl, n-heptyl, N-octyl, n-nonyl, n-decyl, neo-pentyl, 2,4-dimethyl-3-pentyl, 2-heptyl, 3-heptyl, 2-methyl-2-heptyl, 3-methyl-2-hetyl, 4-heptyl, 2,6-dimethyl-4-heptyl, 4-ethyl-4- heptyl, 2-methyl-1-heptyl, 4-methyl-4-heptyl, 3-methyl-1-heptyl, 4-propyl-4heptyl, 4-methyl-1-heptyl, 2,2,3,3-tetramethyl butyl, 2,3-dimethyl pentyl, 2,2,4-trimethyl-pentyl, 2,4-dimethyl-3-ethyl, 3-hexyl, 2-ethyl-hexyl, 2-butyl, t.-butyl, 2-methyl-1-butyl, 2-pentyl, 3-pentyl, 3-methyl-2-butyl, 2-methyl-2-butyl, 2-methyl-1-pentyl, 3-methyl-1-pentyl, 4-methyl-1-pentyl, 2-ethyl-1-butyl, t.amyl, 2,3-dimethyl-1-butyl, 2-hexyl, 3-hexyl, 3-methyl-2-pentyl, 2,2-dimethyl-3-butyl, 4-methyl-2-pentyl, 2,3-dimethyl-2-butyl, 2-methyl-3-pentyl, and 3-methyl-3-pentyl and 3-methyl-2-pentyl.

Preferably the reaction of γ-haloacetoacetic ester with a prepared aqueous trimethylamine solution is carried out at a temperature between 5° and 30° C. (most preferably between 5° and 15°C.).

The aqueous trimethylamine solution is preferably in concentrations of 20 to 50 percent.

The trimethylamine must be used in excess. The quantity which is used is preferably so large that 1 (or say 1.1) to 10, and most preferably 2 to 6 moles (equivalents), of trimethylamine is used per mole (equivalent) of γ-haloacetoacetic ester.

The aqueous solution of trimethylamine is brought to the reaction temperature, e.g., 10°C., and the γ-haloacetoaceitc ester is dosed in slowly. Preferably the dosing-in speeds of 0.02 to 0.2 equivalents (moles) of the prepared trimethylamine quantity per hour, are used. The reaction temperature for the trimethyl amine and the γ-haloacetoacetic ester is preferably between 0° and 50° C.

The excess trimethylamine is distilled off, preferably under vacuum, and the solution obtained is adjusted to a pH of 4to 8. Preferably the solution is subsequently filtered and the solution is fed to the catalytic hydrogenation step. Advantageously paltinum on activated charcoal, nickel (Raney nickel) or ruthenium on activated charcoal is used as the hydrogenation catalyst.

Preferably the hydrogenation temperatures lie between 0° and 70° C. The $H_2$ pressures during the hydrogenation step can be up to and above 100 atm., but is preferably between 2 and 50 atm.

In the case of using platinum or ruthenium as the catalyst, preferably a temperature between 0° and 30°C is used. In the case of nickel, the temperature is preferably raised to between 40° and 70° C.

In general, the yields are better, the higher the $H_2$ pressures are. In the case of more elevated temperatures, the yields drop because of hydrogenolytic splitting of the trimethyamino group.

In this specification, including the claims, all parts, ratios, weights and proportions are on a weight basis, unless otherwise stated or unless otherwise obvious to one ordinarily skilled in the art.

EXAMPLE 1

In a 1 liter flask with a cooling jacket and a drainage cock, equipped with a mechanical stirrer and a thermometer, 278.16 gm. of aqueous trimethylamine solution (TMA) (42.5 percent, 2.00 moles) was prepared and was cooled to 10° C. With a "perpex" hose-equipped compression pump and a teflon hose, which submerged (extended) into the TMA solution, 67.68 gm. of γ-chloroacetoaacetic ethyl ester (97.7 percent, 0.402 moles) was added in doses during 3 hours at 10° C., while stirring well. The vessel and the line were subsequently flushed with 5 gm. of ethanol. The yellowish reaction solution was evaporated on a rotavapor to half its volume - the excess TMS was condensed out with two cooling traps and was recaptured. The pH of the solution was adjusted with some concentrated hydrochloric acid from 7.8 to 6.0, and was filtered off from a yellow precipitate. The brown reaction solution was hydrogenated with 2.2 gm. of platinum on activated charcoal in a 1 liter laboratory autoclave (V4A) during 5 hours at 10° C. 10 atm. and 750 rpm. The solution was filtered off from the catalyst and the resultant bright yellow solution was adjusted to pH 3.0. After the addition of about 10 ml of concentrated hydrochloric acid, the solution was heated during 1.5 hours in a distillation apparatus (at most the pH was 0.5) using a small "Vigreux" column and distillation arch to 100° C. so that the alcohol formed was distilled off. Subsequently, the slution was evaporated on a rotavapor until dry and was dried in the high vacuum over night at 40° C. The dried residue was suspended in 330 ml of absolute ethanol at 0° C., whereby the TMA HCl dissolved and the carnitine hydrochloride was obtained as a colorless crystalline powder. The carnitine hydrochloride was filtered off and was dried until constant in weight. 74.07 gm. of carnitine hydrochloride, with a melting point of 198° to 199° C., was obtained - this corresponded to a yield of 92.2 percent, related to the starting γ-chloroacetoacetic ethyl ester.

EXAMPLE 2

In a 1 liter flask with a cooling jacket equipped with a mechanical stirrer and a thermometer, 295.5 gm. of aqueous trimethylamine solution (TMA) (40.0 percent, 2.00 moles) was prepared and cooled to 10° C. (in a cryometer, or tap water). With a hose-equipped perpex compression pump and a teflon hose, which was submerged (extended) into the TMA solution, 73.50 gm. of γ-chloroacetoacetic ethyl ester (89.6 percent, 40 moles) was added in doses during 3.5 hours at 10° C., while stirring well. The vessel and the teflon hose were flushed with 5 gm. of ethanol. After 1 hour of continued stirring, the excess TMA was sucked off on a rotavapor and condensed. The reaction solution was adjusted from pH 7.5 to pH 6.0 (using 11 ml of concentrated HCl). The brown solution was reacted with 2.2 gm. of platinum on activated charcoal (ex Fluka, 5% purest) and was hydrogenated in a 1 liter SFS laboratory autoclave during 5 hours at 10° C., 10 atm. and 750 rpm. The solution was filtered off from the catalyst. The resultant bright yellow solution was hydrolyzed with approximately 10 ml of concentrated hydrochloric acid (at most the pH was 0.5) in distillation apparatus. Subsequently this was evaporated to dryness and the residue was dried at 40° C. under high vacuum. The residue was suspended in 330 ml of absolute ethanol during 1.5 hours, was filtered and dried to a constant weight. 72.55 gm. of carnitine hdrochloride, with a melting point of 198° to 199° C, were obtained - this corresponded to a 90.5 percent yield, related to the starting γ-chloroacetoacetic ethyl ester.

EXAMPLE 3

In a 300 ml Schmizo double-walled vessel, equipped with a mechanical stirrer and thermometer, 148.0 gm. of aqueous trimethylamine solution (TMA) (40 percent) was prepared and cooled to 10° C. 30.48 gm. of γ-chloroacetoacetic acid methyl ester (98.8 percent, 0.200 mole) was added in doses with a perpex compression pump equipped with a hose at 10° to 11° C, within about 2 hours. The vessel and the dosing-in hose were flushed with 5 ml of absolute ethanol. One hour after addition, the excess TMA was sucked off on a rotavapor under a reduced pressure. The dimethylsuccinylosuccinate (260 mg) formed as a by-product was filtered off and the pH of the solution was adjusted, by means of 9 ml of concentrated hydrochloric acid, from 8.0 to 6.0. The solution was hydrogenated in a SFS laboratory autoclave by means of 1.8 gm. of platinum on activated charcoal (ex Fluka, purest, 5 percent) at 10° atm., and 750 rpm during 5 hours. The catalyst was filtered off. The pH of the reaction solution was adjusted from 8.3 to 0.5 by means of 9 ml of concentrated hydrochloric acid. The solution was heated during 3 hours up to reflux by slow distilling off of methanol-water. subsequently the solution was evaporated on a rotavapor at 50° C and reduced pressure to dryness. The residue was suspended in 140 ml of absolute ethanol at 0° C., was filtered and was dried under vacuum at 50° C during 4 hours.

35.37 gm. of carnitine hydrochloride, with a melting point of 197.5 to 198.5° C, was obtained. It had a content of 97.4 percent, corresponding to 34.45 gm of carnitine hydrochloride, 100 percent, and to a 87.4 percent yield, related to the 100 percent $\gamma$-chloroacetoacetic acid methyl ester 100 percent.

EXAMPLE 4

In a 300 ml Schmizo double-walled vessel, equipped with a mechanical stirrer and thermometer, 148.00 gm. of aqueous trimethylamine solution (TMA) (40 percent) was prepared and cooled to 10° to 11° C. 36.38 gm. of $\gamma$-chloroacetoacetic acid isopropyl ester (98.2 percent, 0.20 mole) was added in doeses by means of a perpex hose-equipped compression pump at 10° to 11° C. within about 2 hours. The vessel and the apparatus for dosing in were flushed with 5 ml of absolute ethanol. One hour after the addition, excess TMA was removed on a rotavapor under reduced pressure. The pH of the solution was adjusted by means of 9 ml. of concentrated hydrochloric acid from 8.2 to 6.0. In a SFS laboratory autoclave, the solution was hydrogenated by way of 1.8 gm of platinum on activated charcoal.(ex Fluka, purest, 5 percent) during 4 hours. The catalyst was filtered off. The pH of the reaction solution was adjusted from 8.4 to 6.5 with the help of 9.5 ml of concentrated hydrochloric acid. The solution was hydrolyzed as usual in a distillation apparatus during 2.5 hours. Subsequently, this was evaporated to a constant weight on a rotavapor under reduced pressure. The residue was suspended in 140 ml of absolute ethanol at 0° C. during 1,5 hours, was filtered and was dried to a constant weight under high vacuum at 40° C during 6 hours.

34.75 gm. of carnitine hydrochloride, with a melting point of 198° to 199° was obtained. It had a content of 98.4 percent, corresponding to 34.19 gm. of carnitine hydrochloride 100 percent, and to a 86.5 percent yield, related to 100 percent $\gamma$-chloroacetoacetic isopropyl ester 100 percent.

EXAMPLE 5

In a 300 ml Schmizo double-walled vessel, equipped with a mechanical stirrer and thermometer, 148.00 gm of aqueous trimethylamine solution (TMA) (40 percent) was prepared and cooled to 10° C. 33.31 gm. of $\gamma$-chloroacetoactic acid ethyl ester (98.8 percent, 0.200 mole) was added in doses with a perpex hose-equipped compression pump at 10° to 11° C within 2 hours. The vessel and the line were flushed with 5 ml of absolute ethanol. One hour after the addition, the excess TMA was removed in the rotavapor, was filtered. The pH of the solution was adjusted to 5.0. The solution was reacted with 4.5 gm. of Raney nickel (ex Fluka, moist) and was hydrogenated overnight (19 hrs.) at 45° C., 50 atm. and 150 rpm. The ph of the solution was 6.2 after hydrogenation. The catalyst was filtered off. The reaction solution was adjusted to a pH of 0.5 with 4 ml of concentrated hydrochloric acid. The solution was heated to reflux during 2.5 hours and was evaporated to a constant weight in a rotavapor at 50° C. The residue was suspended in 140 ml of absolute ethanol at 0° C. during 2, hours, was filtered and was dried under vacuum overnight at 50° C.

34.40 gm of carnitine hydrochloride, with a melting point of 196° to 197° C. was obtained. It had a content of 98.9 percent, corresponding to 34.02 gm. of carnitine hydrochloride 100 percent, and to a 86.1 percent yield, related to 100 percent $\gamma$-chloroacetoacetic ester 100 percent.

EXAMPLE 6

In a 300 ml Schmizo double-walled vessel, equipped with a mechanical stirrer and thermometer, 148.00 gm. of aqueous trimethylamine solution (TMA) (40 percent) was prepared and was cooled to 10° C. 43.60 gm. of $\gamma$-bromoacetoacetic acid ethyl ester (93.6 percent, 0.200 mole) was added in doses with the aid of a perpex hose-equipped compression pump within 2 hours. The vessel and the dosing in hose were flushed with 5 ml of absolute ethanol. One half hour after the addition, the excess TMA was removed in a rotavapor. The pH of the solution was adjusted from 8.0 to 6.0 with the help of 10 ml concentrated hydrochloric acid. The solution was reacted with 1.8 gm. of platinum on activated charcoal (ex Fluka, purest, 5 percent) and was hydrogenated at 10° C., 10 atm. and 1500 rpm during 5 hours. The catalyst was filtered off. The pH of the solution was adjusted from 7.4 to 0.5 with the help of 6 ml of concentrated hydrochloric acid and was hydrolyzed during 2.5 hours in a distillation apparatus. Subsequently, it was evaporated to dryness to 62.47 gm and the residue was suspended in 150 ml of absolute ethanol at 0° C. The solution was filtered and the residue was suspended in 150 ml of absolute ethanol at 0° C. The solution was filtered and the residue was dried to a constant weight. A mixture of carnitine hydrobromide and carnitine hydrochloride was obtained.

What is claimed is:

1. The process for the production of carnitine hydrochloride which comprises: (a) placing an ester of $\gamma$-haloacetoacetic acid having the formula:

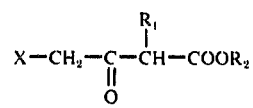

wherein $R_1$ is hydrogen, $R_2$ is a lower alkyl group having 1 to 10 carbon atoms and X is a halogen atom selected from the group consisting of chlorine or bromine, in an aqueous solution of excess trimethyl amine held at a temperature between 0° and 50° C., a reaction resulting between said ester and said amine; (b) distilling off the excess trimethyl amine; (c) adjusting the pH of the solution to between 4 and 8, (3-carbalkoxy-2-oxopropyl)-trimethyl ammonium halide resulting; (d) catalytically hydrogenating said (3-carbalkoxy-2-oxopropyl)-trimethyl ammonium halide without isolating said halide from solution, a carnitine ester resulting; and (e) converting said carnitine ester by means of aqueous hydrochloric acid into said carnitine hydrochloride, which has the formula:

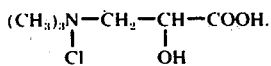

2. The process of claim 1 wherein said step (a) is conducted at a temperature between 5° and 30° C.

3. The process of claim 1 wherein said step (b) is conducted at a temperature between 5° and 15° C.

4. The process as described in claim 1 wherein said aqueous solution of trimethylamine has a content of trimethylamine of 20 to 50 percent.

5. The process as described in claim 1 wherein 1 to 10 moles of trimethyl amine is used per mole of said γ-haloacetoacetic ester.

6. The process as described in claim 1 wherein 20 to 6 moles of said trimethyl amine is used per mole of said γ-haloacetoacetic ester.

7. The process as described in claim 1 wherein said γ-halogen acetoacetic ester is added in doses at a speed of 0.02 to 0.02 equivalents of the prepared trimethylamine quantity per hour.

8. The process as described in claim 1 wherein said excess trimethylamine is distilled off under vacuum.

9. The process as described in claim 1 wherein, in step (c), the solution is adjusted to a pH of 5.8 to 6.2.

10. The process as described in claim 1 wherein said hydrogenation is carried out using platinum on activated charcoal, with a temperature between 0° and 50° C. and with an $H_2$ pressure of 2 to 100 atm.

11. The process of claim 1 wherein said hydrogenation catalyst is platinum on activated charcoal.

12. The process of claim 1 wherein said hydrogenation step (c) is conducted at a temperature between 0° and 70° C.

13. The process of claim 1 wherein said hydrogenation step is conducted at a $H_2$-pressure between 2 and 50 atmospheres.

14. The process as described in claim 1 wherein said γ-haloacetoacetic ester is a γ-chloroacetoacetic ester.

* * * * *